(12) United States Patent
Yim et al.

(10) Patent No.: US 7,507,254 B2
(45) Date of Patent: Mar. 24, 2009

(54) INORGANIC BONE GRAFT MATERIALS USING ANIMAL BONE AND METHOD FOR PREPARING THEREOF

(75) Inventors: Chang Joon Yim, Seongnam-si (KR); Se Won Kim, Cheonan-si (KR); Jung Keun Kim, Seongnam-si (KR); Jong Yeo Kim, Cheonan-si (KR); Hyung Gun Kim, Seoul (KR); Dong Ryung Shin, Seoul (KR); Yong Mok Yu, Seongnam-si (KR); Sung Bin Yim, Seongnam-si (KR); Seon Yle Ko, Cheonan-si (KR); Sung Churl Lee, Cheonan-si (KR)

(73) Assignee: Oscotec, Inc., Cheonan-si (KR)

( * ) Notice: Subject to any disclaimer, the term of this patent is extended or adjusted under 35 U.S.C. 154(b) by 360 days.

(21) Appl. No.: 11/162,594

(22) Filed: Sep. 15, 2005

(65) Prior Publication Data
US 2006/0014283 A1    Jan. 19, 2006

Related U.S. Application Data

(63) Continuation-in-part of application No. 10/130,455, filed on May 16, 2002, now abandoned.

(51) Int. Cl.
*A61F 2/28*    (2006.01)
(52) U.S. Cl. ............... 623/16.11; 623/23.61; 623/23.63; 424/489
(58) Field of Classification Search ........................ None
See application file for complete search history.

(56) References Cited

U.S. PATENT DOCUMENTS

| | | | | | |
|---|---|---|---|---|---|
| 4,257,405 | A | * | 3/1981 | Colville | 128/898 |
| 4,440,750 | A | * | 4/1984 | Glowacki et al. | 424/572 |
| 4,743,259 | A | * | 5/1988 | Bolander et al. | 128/898 |
| 4,781,721 | A | * | 11/1988 | Grundei | 164/34 |
| 5,073,373 | A | * | 12/1991 | O'Leary et al. | 424/422 |
| 5,306,302 | A | * | 4/1994 | Bauer et al. | 623/23.63 |
| 5,513,662 | A | * | 5/1996 | Morse et al. | 128/898 |
| 5,693,615 | A | * | 12/1997 | Stone | 514/12 |
| 5,776,193 | A | * | 7/1998 | Kwan et al. | 424/423 |

OTHER PUBLICATIONS

Hsu et al, "Bone Grafts and Implants," Spine Care, vol. 2, 1995. www.spine-dr.com/site/surgury/s_bone_grafts.html accessed Sep. 16, 2004.*
Dictionary.com "Turbinate Bone" accessed Sep. 15, 2004.*
On-line Medical dictionary "Spongy bone" accessed Sep. 15, 2004 http://cancerweb.ncl.ac.uk/cgi-bin/omd?*
Lenntech Disinfectants, "Sodium hypochlorite" accessed Sep. 16, 2004 http://lenntech.com/water-disinfection/disinfectants-sodium-hypochlorite.htm.*
Lenntech "Hydrogen Peroxide" accessed Sep. 16, 2004 http://lenntech.com/water-disinfection/disinfectants-hydrogen-peroxide.htm.*
Nakamura et al, Oral Surg Oral Med Oral Pathol, 1985, vol. 60, No. 3, pp. 322-326.*
Rabie, A.B.M. et al., "The Effect of Demineralized Bone Matrix on the Healing of Intramembranous Bone Grafts in Rabbit Skull Defects", J. Dent. Res., 75(4), Apr. 1996, pp. 1045-1051.
Wada, Takashi et al., "Autogenous, Allogenic and Beta-TCP Grafts: Comparative Effectiveness in Experimental Bone Function Defects in Dogs", J. Oral Implantol., vol. XV, No. 4, 231-236 (1989).
Zhang, Min et al., "Effects of Demineralization Process on the Osteoinductivity of Demineralized Bone Matrix", J. Periodontol., Nov. 1997, pp. 1085-1092, vol. 68, No. 11.
Hsu et al., "Bone Grafts and Implants", Spine Care, vol. 2, 1995, pp. 1-21.
Dictionary.com, "Turbinate Bone" accessed Sep. 15, 2004.
On-line Medical dictionary, "Spongy bone," accessed Sep. 15, 2004, http://cancerweb.ncl.ac.uk/cgi-bin/omd?
Lenntech Disinfectants, "Sodium hypochlorite," accessed Sep. 16, 2004, http://lenntech.com/water-disinfection/disinfectants-sodium-hypochlorite.htm.
Lenntech "Hydrogen Peroxide," accessed Sep. 16, 2004, http://lenntech.com/water-disinfection/disinfectants-hydrogen-peroxide.htm.
Nakamura et al., Oral Surg. Oral Med. Pathol., 1985, vol. 60, No. 3, pp. 322-326.
Rabie, A.B.M. et al., "The Effect of Demineralized Bone Matrix on the Healing of Intramembranous Bone Grafts in Rabbit Skull Defects", *J Dent Res*, 75(4), Apr. 1996, pp. 1045-1051.
Wada, Takashi et al., "Autogenous, Allogenic, and β-TCP Grafts: Comparative Effectiveness in Experimental Bone Furcation Defects in Dogs", *Journal of Oral Implantology*, vol. XV, No. Four, 1989, pp. 231-236.
Zhang, Min et al, "Effect(s) of the Demineralization Process on the Osteoinductivity of Demineralized Bone Matrix", *J. Periodontol*, Nov. 1997, pp. 1085-1092.

* cited by examiner

*Primary Examiner*—L Blaine Lankford
*Assistant Examiner*—Allison M. Ford
(74) *Attorney, Agent, or Firm*—Lucas & Mercanti, LLP (57) ABSTRACT

The present invention relates to inorganic bone graft materials and a method for preparing the bone graft materials. Particularly, the present invention relates to a method for preparing bone graft materials comprises the following steps: collecting cancellous bones from an animal; removing lipids and organic materials from the cancellous bones using organic solvent, sodium hypochlorite and hydrogen peroxide; and sterilizing the cancellous bones wherefrom the lipids and the organic materials are removed. The bone graft materials prepared by the method of the present invention meet requirements for use in bone grafting, including biocompatibility, sterilization, osteoinductivity and osteoconductivity with free from immunogenecity and toxicity to tissue and are suitable for use in osteogenesis and have morphogenesis.

5 Claims, 4 Drawing Sheets

INORGANIC BONE GRAFT MATERIALS USING ANIMAL BONE AND METHOD FOR PREPARING THEREOF

FIELD OF THE INVENTION

The present invention relates to inorganic bone graft materials and a method for preparing thereof.

Particularly, the present invention relates to the method for preparing inorganic bone graft materials comprising the following steps: collecting cancellous bone from an animal; removing lipids and organic materials such as collagens from the cancellous bone using organic solvent, sodium hypochlorite and hydrogen peroxide; and sterilizing the cancellous bone wherefrom lipids and organic materials are removed.

The bone graft materials prepared by the manufacturing process of the present invention meet requirements for use in bone grafting, including biocompatibility, sterilization, osteoinductivity and osteoconductivity without immunogenecity and toxicity to tissue and are suitable for use in osteogenesis and bone morphogenesis

BACKGROUND

Bony tissues are connective tissues consisting of bone cells and extracellular matrices, but are different from other connective tissues in that the ossified connective substances within the extracellular matrices are inorganic. The inorganic substance consists mainly of calcium phosphate which exists as hydroxyapatite crystals ($Ca_{10}(PO_4)(OH)_2$).

Bony tissues are hard enough to support and defend against physical stresses of the body, and their fracture or their density reduction or damage attributed to pathogenic changes may cause the body to suffer from deformity. When damaged or removed owing to any reasons, a bone has to be regenerated naturally or needs to be substituted with a prosthesis or a bone material from another body part by surgery. In addition, healing a physically broken (fractured) bone or a surgically damaged bone requires using various prosthetic tools, including artificial bones, for artificially relaying and immobilizing the bone. In this case, however, it takes a significantly long period of time for the bone to recover to its original figure and function while the patient suffers from serious physical and mental stresses. Further, as the healing procedure becomes long, the damaged part is increasingly apt to be under the danger of infection with germs, so that a perfect remedy may not be expected.

It remains an urgent need to develop methods for facilitating the medical treatment process (regeneration) of damaged bony tissues or inducing the morphogenesis of new bony tissues, or materials suitable for such treatment process. In connection, various selective materials such as bioceramics, composite materials and bone derivatives, as well as artificial fillers for bone recovery, such as natural or synthetic polymers have been developed.

Substitution of damaged bony tissues is also being undertaken by facilitating osteogenesis with various bone onlays and bone graft substitutes. Application of bone onlays and bone graft substitutes is conducted largely by two methods: an autograft method and an allograft method. Both of the two methods utilize human's bones to induce osteogenesis. The bones to be grafted must be similar in elastic modulus to bones adjacent to the graft area because graft materials greatly different in elastic modulus, e.g., metal grafts generate excess stresses.

However, grafting methods utilizing bone onlays also suffer from several problems. When adopting an autograft method, the grafts to be available are quantitatively limited. In addition, while a surgical operation is conducted to extirpate a required bone for autograft, it may be in danger of bacterial infection and loss of blood all at times. In addition, the areas wherefrom grafts are extirpated become poor in structural stability. The grafting technique, including the surgery operation, may force some patients to endure pain for a longer period of time than does fusion surgery. The allograft method has an advantage over the autograft method in that supply of allografts can be relatively achieved because they are obtained from allo-donators, but allogenic bones are far inferior in osteoinductive potential to autogenous bones and thus, can be used as only temporary supports.

Additional problems are also found in both the autograft and the allograft methods. For instance, since the grafts alone, used in the above graft methods, cannot offer stability enough to endure the spinal marrow, an internal fixing method needs to be conducted concurrently. In this case, metal fixing means are used, requiring a more complicated surgical operation. In addition, the operator must repeatedly trim the graft into a precise size to fit into a targeted bony tissue, which results in extending the time it takes for the surgical operation. Further, in general, a smooth surface of a graft cannot provide a frictional force necessary for the graft to fix between adjacent bony tissues. Thus, the trimming may be in danger of slipping of the trimmed graft from the bony tissues, breaking the structure of the grafted bony tissue and causing damage to the nerve system and the vascular system near the bony tissue.

In order to meet the necessity of safer and more convenient bone grafts, keen interest has recently been taken in bone graft substitutes, such as bioceramics. Calcium phosphate ceramics, one of the bioceramics, exhibit superior biocompatibility and are significantly free from the bacterial infection and immunological danger which may be caused upon allograft. Moreover, with the above advantages of allografting-bone grafts, calcium phosphate ceramics can be produced in abundance. In addition, such bioceramics are not only osteoconductive, but provide porous matrices which facilitate bone morphogenesis in bony tissues. However, bioceramics are disadvantageous in that internal fixation is required before grafting because their strength is too low to support the weight of the spinal marrow.

Development was also achieved on various compositions of medical cements which can be applied in vivo. Among them, healing cements consisting of calcium phosphate possess excellent flexibility because tetracalcium phosphate, a main constituent of calcium phosphate, can be transformed into hydroxyapatite during the healing process. However, the prolonged time period that it takes for these healing cements to cure makes it difficult to apply them in practice. Also, it is difficult to apply the healing cements in tissues where body fluid is abundant, because when the cements are brought into contacting with pseudo-body fluid immediately after forming a kneaded plaster by mixing the cements, the fluid may penetrate into and finally destroy the kneaded plaster.

If damaged, various body joints, such as the total hip joint, the total knee joint and the total shoulder joint, may be substituted by artificial bones. Available for this purpose are synthetic materials which are prepared from a mixture of polymethylmetachlorite (PMMA) and benzoilperoxide. The artificial bones prepared from the synthetic materials, however, suffer from the serious problem of being not degraded naturally in vivo. Therefore, newly growing bones are obstructed by the persistent artificial bones, so that a high fever occurs, hurting the neighboring tissues. Conventionally, a patient suffering from a hernia of the cervical spine, lumbar spine, or thoracic spine discs undergoes a surgical operation by use of autografts. To secure his or her own iliac bone, an additional operation must be performed on the patient, which forces him or her to suffer from additional pain and the patient may develop complications. Alternatively, bones taken from corpses, such as the fibula and ilium, are used as substitutes for use in the operation. This allografting operation certainly imposes a physically lighter burden on the patient, but suffers from many disadvantages of more feasible viral infection, poorer strength maintenance of grafts, higher material cost, and poorer biocompatibility. In addition, when allograft providers do not secure sufficient corpses, the supply and demand of allografts is not balanced. Further, allografts find difficulty in keeping bone strength suitable for the patients who suffer from osteoporosis or who undergo an operation on ossa faciei or tops of the odontoid process. Upon allograft, a loosening is apt to happen.

To surmount these defects of bone graft substitutes and manufacturing process of the existing goods and characteristics thereof, these inventors of the present invention have developed novel bone graft materials using animal bone.

SUMMARY OF THE INVENTION

It is an object of this invention to provide a process for manufacturing of bone graft materials using animal bone and bone graft materials therefrom.

In accordance with the present invention, the foregoing objects and advantages are readily obtained.

The present invention provides a method for preparing of inorganic bone graft material comprising the following steps:

1) collecting cancellous bone from an animal;
2) removing lipids and organic materials from the cancellous bone using an organic solvent, sodium hypochlorite and hydrogen peroxide; and
3) sterilizing the cancellous bone wherefrom the lipids and the organic materials are removed.

Further, the present invention provides a method for preparing of inorganic bone graft material comprising the following steps:

1) deep freezing a bone from an animal;
2) removing a compact bone from the bone using bone saw and obtaining a cancellous bone by cutting the cancellous bone into appropriate size;
3) making bone powder by pulverizing the cancellous bone minutely;
4) washing the bone powder using distilled water;
5) removing lipids from the washed bone powder using an organic solvent;
6) drying the bone powder of step 5 to remove organic solvent in the hood, and separating it into above 1.4 mm/1-1.4 mm/0.6-1 mm/0.425-0.6 mm/below 0.425 mm by size;
7) deep freezing the bone powder having size of 0.6-1 mm and 0.425-0.6 mm, and further pulverizing the bone powder bigger than 1 mm minutely;
8) removing lipids from the re-pulverized bone powder of step 7 using the first organic solvent;
9) drying the bone powder of step 8 to remove the first organic solvent in the hood, and separating it into above 1.4 mm/1-1.4 mm/0.6-1 mm/0.425-0.6 mm/below 0.425 mm by size;
10) collecting the bone powder of step 9 having size of 0.6-1 mm and 0.425-0.6 mm and removing the first organic solvent by washing with the second organic solvent;
11) washing the bone powder prepared by steps 7 and 10 with distilled water;
12) removing organic materials from the bone powder by treating the washed bone powder of step 11 with sodium hypochlorite;
13) further removing organic materials from the bone powder of step 12 by treating the bone powder with hydrogen peroxide and keeping the bone powder overnight in hydrogen peroxide;
14) washing the bone powder of step 13 with distilled water;
15) removing moisture of the washed bone powder of step 14 and lyophilizing the bone powder with freeze drier.

This invention also provides an inorganic bone graft material as osteoconductive and osteoinductive substrate material with free from immunogenecity and toxicity to tissue which maintains its original crystal structure and is highly able to promote biocompatible osteogenesis.

Further features of the present invention will appear hereinafter.

DETAILED DESCRIPTION OF PREFERRED EMBODIMENTS

Hereinafter, the present invention is described in detail.

The present invention provides a process for manufacturing of bone graft materials using animal bone.

The method for preparing of inorganic bone graft materials of the present invention comprises the following steps:

1) collecting cancellous bone from animal;
2) removing lipids and organic materials from the cancellous bone using an organic solvent, sodium hypochlorite and hydrogen peroxide; and
3) sterilizing the cancellous bone wherefrom the lipids and the organic materials are removed.

Since the inorganic bone graft materials of the present invention are free from organic materials such as collagens which may induce immune response, any animal can be used for a donator of bones, as long as the cancellous bone is obtainable therefrom.

However, in an embodiment of the present invention, the animal of step 1 is a vertebrate but not limited thereto.

In a preferred embodiment of the present invention, the animal of step 1 is a bovine.

In a more preferred embodiment of the present invention, the animal of step 1 is a one-year dairy cattle.

In another embodiment of the present invention, the organic solvent is diethyl ether or ethanol but not limited thereto.

In still another embodiment of the present invention, the sterilizing of step 3 can be any ordinary sterilizing process such as autoclave, irradiation and gas sterilization. However, in a preferred embodiment, the sterilizing process is irradiation but not limited thereto.

Bone graft materials of the prior arts are prepared by process of removing organic materials and heat treatment. However, the inorganic bone graft materials of the present invention do not take heat treatment, so it still has original crystal structure. It takes different chemical treatment process, so it can also maximize the ability of new bone formation. Since the bone graft materials of the present invention contains only inorganic materials and does not induce immune responses, it can be used for a good frame to make it easier to form new bone structure.

In addition, the present invention provides the bone graft materials manufactured by the process using animal bone.

The bone graft materials of the present invention meet requirements for use in bone grafting, including biocompatibility, sterilization, osteoinductivity and osteoconductivity with free from immunogenecity and toxicity to tissue and are suitable for use in osteogenesis and bone morphogenesis Further, the present invention provides a method for preparing inorganic bone graft materials comprising the following steps:

1) preparing a bone from an animal;
2) removing a compact bone from the bone using bone saw and obtaining a cancellous bone;
3) making bone powder by pulverizing the cancellous bone of step 2 minutely;
4) washing the bone powder with distilled water;
5) removing lipids from the washed bone powder using the first organic solvent;
6) removing the first organic solvent from the bone powder of step 5 using the second organic solvent;
7) washing the bone powder of step 6 in order to remove the second organic solvent using distilled water;
8) removing organic materials from the bone powder of step 7 using sodium hypochlorite and hydrogen peroxide;
9) washing the bone powder of step 8 using distilled water;
10) lyophilizing the bon powder of step 9 with freeze drier.

In a preferred embodiment of the present invention, the animal is a vertebrate but not limited thereto.

In a preferred embodiment of the present invention, the distilled water of step 4, 7 and 9 is double distilled water but not limited thereto.

In a preferred embodiment of the present invention, the first organic solvent is a non-polar organic solvent. In a more preferred embodiment of the present invention, the non-polar organic solvent is ether, chloroform or acetone but not limited thereto. In the most preferred embodiment of the present invention, the ether is diethyl ether.

In a preferred embodiment of the present invention, the second organic solvent is a polar organic solvent. In a more preferred embodiment of the present invention, the polar organic solvent is a lower alcohol such as methanol, ethanol, propanol and butanol. In the most preferred embodiment of the present invention, the second organic solvent is ethanol.

In a preferred embodiment of the present invention, the organic materials of step 8 comprise collagen.

In addition, the present invention provides a method for preparing inorganic bone graft materials comprising the following steps:

1) deep freezing a bone from an animal;
2) removing a compact bone from the bone using bone saw and obtaining a cancellous bone by cutting the cancellous bone into appropriate size;
3) making bone powder by pulverizing the cancellous bone minutely;
4) washing the bone powder using distilled water;
5) removing lipids from the washed bone powder using the first organic solvent;
6) drying the bone powder of step 5 to remove organic solvent in the hood, and separating it into above 1.4 mm/1-1.4 mm/0.6-1 mm/0.425-0.6 mm/below 0.425 mm by size;
7) deep freezing the bone powder having size of 0.6-1 mm and 0.425-0.6 mm, and further pulverizing the bone powder bigger than 1 mm minutely;
8) removing lipids from the re-pulverized bone powder of step 7 using the first organic solvent;
9) drying the bone powder of step 8 to remove the first organic solvent in the hood, and separating it into above 1.4 mm/1-1.4 mm/0.6-1 mm/0.425-0.6 mm/below 0.425 mm by size;
10) collecting the bone powder of step 9 having size of 0.6-1 mm and 0.425-0.6 mm and removing the first organic solvent by washing with the second organic solvent;
11) washing the bone powder prepared by steps 7 and 10 with distilled water;
12) removing organic materials from the bone powder by treating the washed bone powder of step 11 with sodium hypochlorite;
13) further removing organic materials from the bone powder of step 12 by treating the bone powder with hydrogen peroxide and keeping the bone powder overnight in hydrogen peroxide;
14) washing the bone powder of step 13 with distilled water;
15) removing moisture of the washed bone powder of step 14 and lyophilizing the bone powder with freeze drier.

In an embodiment of the present invention, the animal of step 1 is a vertebrate but not limited thereto.

In a preferred embodiment of the present invention, the animal of step 1 is a bovine.

In a more preferred embodiment of the present invention, the animal of step 1 is a one-year dairy cattle.

In an embodiment of the present invention, the cancellous bone of step 2 has sizes between 1 mm×1 mm×1 mm and 30 mm×30 mm×30 mm. In a preferred embodiment of the present invention, the bone powder of step 3 is pulverized by bone mill and micromill minutely.

In a preferred embodiment of the present invention, the first organic solvent or the steps 5 and 8 is a non-polar organic solvent such as ether, acetone and chloroform but not limited thereto. In a more preferred embodiment of the present invention, the first organic solvent is diethyl ether.

In a preferred embodiment of the present invention, the second organic solvent of the step 10 is a polar organic solvent such as lower alcohol. In a more preferred embodiment of the present invention, the second organic solvent is ethanol.

In a preferred embodiment of the present invention, the distilled water of steps 4, 11 and 14 is double distilled water.

After washing the bone powder with distilled water, sodium hypochlorite and hydrogen peroxide are treated in order to remove organic materials such as collagens from the bone powder.

In a preferred embodiment of the present invention, the concentration of sodium hypochlorite is 0.1 to 2% and the concentration of hydrogen peroxide is 1 to 5%. In a more preferred embodiment of the present invention, the concentration of sodium hypochlorite is 0.5% and the concentration of hydrogen peroxide is 3.5.

Figure 1:
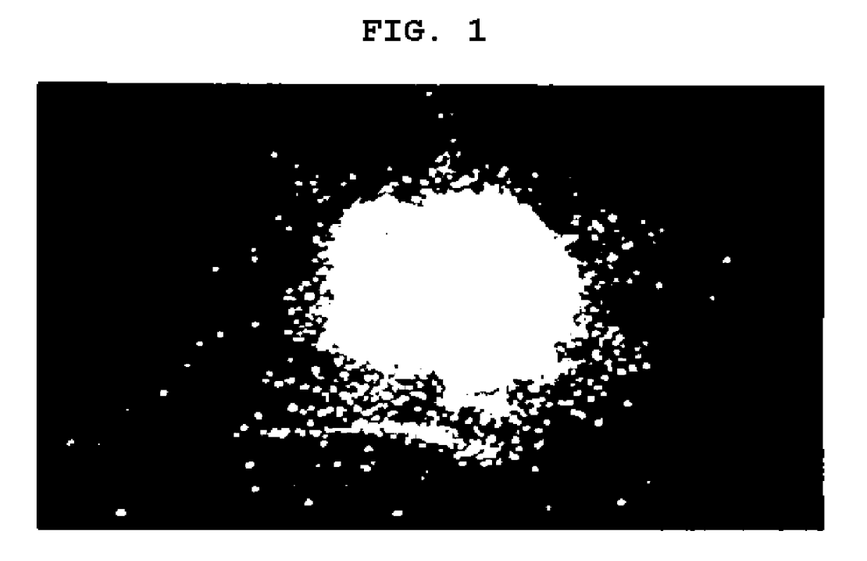
FIG. 1 is a photograph of bone powder prepared by a process for manufacturing bone graft materials of the present invention.

A photograph of the bone powder prepared by the process is represented in FIG. 1.

The present inventors have performed experiments for preparing inorganic bone powder and its stability test (acute toxicity test, cell growth inhibition test, graft test, sensitization test, aseptic test) as follows.

To test the safety of the bone powder of the present invention, acute and sub-acute toxicity were monitored in the mice by observing death rate and strange behavior patterns such as autonomic movement, offensivity, atypical movement, and sleeping problem.

As a result, there were no dead mice or mice showing changes in behavior pattern, so it had been demonstrated that bone powder extract of the present invention had no acute and sub-acute toxicity to the animals used in the experiment.

To test the safety of bone powder of the present invention, effects of extract of the bone powder to cell growth and an inhibition was observed by culturing the cells with medium containing the bone powder extract.

As a result, cell growth inhibition rate was −18.7%, so the bone graft materials of the present invention did not inhibit cell proliferation and rather promoted cell proliferation.

To observe whether the graft materials may raise any local responses at surrounding tissues in the living body, an implantation test was performed.

Sprague-Dawley rats were used and reticular bone fragments therefrom were cut and sterilized by irradiation.

As a result, there were no inflammatory symptoms by optical and microscopic observation. The grafted materials were histologically tegumentalized into the number of cells, exudates, granulation tissues and fibrous tissues (See FIG. 2 and FIG. 3).

The probability of skin sensitization was tested using guinea pigs. In case of intradermal injection, each reagent solution (A, B, C) was injected intradermally to each region (a, b, c) located between both shoulder blades of shaved each guinea pig (See FIG. 4).

As a result, edema of grade 1 was found at the 2 of 20 in A region, 2 of 20 in B region and 3 of 20 in C region and there were no regions representing erythema. For the control group, edema of grade 1 was appeared at the 2 of 10 in A region, 1 of 10 in B region and 2 of 20 in C region and there were no regions representing erythema.

From these results, it was concluded that there were no sensitization responses induced by the bone power extract of the present invention during the topical induction phase.

After the topical induction phase test, the challenge phase was performed.

As a result, there were no edema and erythema in all animals during the challenge phase test. So, it was confirmed that there was no sensitization reaction induced by the bone powder extract of the present invention during the challenge phase. So, it was concluded that there was little inducing probability of the sensitization reaction by the reagent solution of the present invention, since there was no sensitization reaction in the present experiment of maximization sensitization test constituting intradermal induction phase, topical induction phase and challenge phase.

To confirm the safety and effectiveness of the bone powder, aseptic test was performed to check for the existence of any bacteria or fungi proliferation. From the test of biological safety and efficiency of the reagent solution in the present invention by detecting microorganisms, there could not be found any microorganism in the reagent materials.

Therefore, it was concluded that the reagent solution of the present invention was suitable for application according to aseptic test.

EXAMPLES

Practical and presently preferred embodiments of the present invention are illustrative as shown in the following examples.

However, it will be appreciated that those skilled in the art, on consideration of this disclosure, may make modifications and improvements within the spirit and scope of the present invention.

Example 1

Bone Powdering Procedure

Leg bones extracted from 1 year-old dairy cattle were stored at deep freezer. A compact bone was removed from the stored leg bone using bone saw, and cancellous bone was cut by the size of 5 mm×5 mm×5 mm. The cancellous bone was pulverized using bone mill, and bone powder was minutely ground using micromill for 1 min. The bone powder was washed with secondary distilled water 3 times each for 1 hour. Lipid of the washed bone powder was removed by washing with an organic solvent, diethyl ether 2 times each for 4 hours, and the bone powder was soaked in diethyl ether until next day morning. After removing diethyl ether and drying the bone powder in the hood, the bone powder was divided into above 1.4 mm/1-1.4 mm/0.6-1 mm/0.425-0.6 mm/below 0.425 mm by the size using sieve.

The bone powder of the size 0.6-1 mm and 0.425-0.6 mm were stored in a deep freezer, and the bone powder having bigger than objective size (0.6-1 mm/0.425-0.6 mm) was minutely ground using micromill for 1 min. After removing lipid of the re-ground bone powder using diethyl ether 2 times each for 4 hours, the bone powder was soaked in diethyl ether until next morning. After removing the organic solvent and drying the bone powder in the hood, the bone powder was divided by the size using sieve. The bone powder was collected by the size and washed with ethanol 2 times each for 1 hour to remove the diethyl ether. The bone powder was washed 3 times each for 1 hour with secondary distilled water. The bone powder was treated with 0.5% NaOCl 2 times each for 1 hour. And then, the bone powder was treated with 3.5% $H_2O_2$ 2 times each for 1 hour and kept in the 3.5% $H_2O_2$ overnight. The bone powder treated with $H_2O_2$ was washed with secondary distilled water for 3 days. After washing and removing, the bone powder was frozen in freezer and lyophilized using freezer drier.

A photograph of the bone powder prepared by the steps is represented in FIG. 1.

Example 2

Safety Test of Bone Powder

To test the safety of the bone powder prepared by the Example 1, the following experiments were performed.

<2-1> Acute Toxicity Test

After injecting 0.15 ml of extract of the bone powder (20%) prepared by the Example 1 through tail vein of mice, acute and sub-acute toxicity of the bone powder were monitored by observing death rate and strange behavior pattern of the mice according to time. The intravenous injection of the present experiment was followed by the rules of ASTM F750 in case of acute toxicity test and OECD Guideline No. 409 in case of sub-acute toxicity test.

<2-1-1> Reagent

Extract of the bone powder was prepared by extracting 4 g of the bone powder prepared by the Example 1 with 20 ml of saline as extraction solvent and incubating with shaking for 72 hours at 37° C. water bath.

<2-1-2> Sample Group 5 male mice having about 30 g of body weight per one group was used for test.

After injection of the bone powder extract prepared by Example 2-1-1 or saline as control, death rate and strange behavior pattern of each group were monitored at immediately after injection, after 1 hour, 3 hours, 24 hours (acute), 48 hours, 72 hours and 7 days (sub-acute).

<2-1-3> Method

After injection of the bone powder extract or saline through the tail vein of mice in the ratio of 5 ml reagent per 1 kg body weight, i.e. 0.15 ml per each mouse, it was compared with the control whether death rate and any changes in the behavior pattern such as autonomic movement, offensivity, atypical movement, and sleeping problem were occurred.

As a result of observing animals at immediately after injection, after 1 hr, 3 hr, 24 hr, 48 hr, 72 hr and 7 days, there were no mice being dead or showing changes in behavior pattern.

TABLE 1

Result of injection (○: alive, X: dead)

| | Group | | | | |
|---|---|---|---|---|---|
| | 1 | 2 | 3 | 4 | 5 |
| Control | ○ | ○ | ○ | ○ | ○ |
| Immediately | ○ | ○ | ○ | ○ | ○ |
| 1 hour | ○ | ○ | ○ | ○ | ○ |
| 3 hours | ○ | ○ | ○ | ○ | ○ |
| 24 hours | ○ | ○ | ○ | ○ | ○ |
| 48 hours | ○ | ○ | ○ | ○ | ○ |
| 72 hours | ○ | ○ | ○ | ○ | ○ |
| 7 days | ○ | ○ | ○ | ○ | ○ |

As described in the above result, it was demonstrated that the bone powder extract of the present invention had no acute and sub-acute toxicity to the animals used in the experiment. This means that the bone powder of the present invention is safe for bone grafting.

<2-2> Growth Inhibition Test to the Cultured Cell Lines

To test the safety of the bone powder of the present invention, effects of the bone powder extract to cell growth and inhibition were observed by culturing a mouse fibroblast cell line, L929 with medium containing the bone powder extract.

<2-2-1> Test Materials

A mouse fibroblast cell line, L929 (ATCC Accession No: CCL-1), originated from mouse connective tissues was used for test and cultured in the MEM medium containing 10% FBS by conventional cell culturing method. L929 cell line was cultured on the flask of 75 cm² area and the medium was changed twice a week. After formation of cell monolayer, cells were subcultured in the ratio of 1:10. The incubation was performed at 37° C. and 95% humidity with continuous supply of 5% $CO_2$ and 95% atmosphere.

<2-2-2> Method

The mouse fibroblast cell line, L929, proper to toxicity test was used for growth inhibition test and cultured in the MEM medium with 10% FBS. After collecting cells by treatment of trypsin-EDTA solution to the monolayered cells on flask and counting the number of cells, cell suspension was prepared by adjusting the cell density into 1×10⁶ cell/ml.

An extract-treated medium was prepared by mixing the bone powder extract prepared by Example 2-1-1 with twofold concentration of culture medium equally, and a control medium by mixing the distilled water and twofold concentration of culture medium equally. 0.2 ml (2×10⁵ cells) of cell suspension was added into 15 tubes and then 5 tubes of them were treated with 2 ml of sample medium and the others were treated with 2 ml of control medium. 5 tubes among 10 tubes containing the control medium were centrifuged to remove the culture medium and then cells were re-suspended with phosphate-buffered saline (PBS, pH 7.0). The cell suspension was washed with PBS two times, centrifuged and stored at 4° C. It was used as the control group on the reaction initiation. The cells in 10 tubes of the sample and the control group of 72 hours were transferring into 24-well flask and incubated for 72 hours at 5% $CO_2$ incubator. After cultivation, the cells were collected, washed with 2 ml of PBS (pH 7.0) three times, and used as the sample and the control group of 72 hours, respectively.

After destruction of cells in the sample and the control groups, total protein concentration was measured by Lowry method. Total protein concentration and average absorbency (AA) of each group were measured, respectively, and the cell growth inhibition rate (%) was calculated by the following equation:

Growth inhibition rate (%)=1−[{(AA of sample at 72 hours)−(AA of control at the initiation)}/{(AA of sample at 72 hours)−(AA of control at the initiation)}]×100

The results measured by the method were as following:

Average absorbency of the sample (72 hr): 0.745

Average absorbency of the control group (72 hr): 0.675

Average absorbency of the control group (reaction initiation): 0.301

Cell growth inhibition rate calculated by the equation was −18.7%, so the bone graft materials of the present invention did not inhibit proliferation of L292 cell line and rather promoted cell proliferation.

<2-3> Transplantation Test

To observe whether the graft materials of the present invention may raise any local responses at surrounding tissues in the living body, transplantation test was performed by optical and microscopic observation.

<2-3-1> Test Animals

8 Sprague-Dawley rats having about 250 g of body weight were used. Animals were fed with conventional solid foods and supplied water unlimitedly.

<2-3-2> Materials

Cancellous bone fragments collected from 1 year-old dairy cattle were treated with an organic solvent in order to remove lipids and then treated with sodium hypochlorite (NaOCl) and hydrogen peroxide ($H_2O_2$) in order to remove organic materials such as collagens. The bone fragments wherefrom the lipids and the organic materials were removed were cut into 1 mm×3 mm×10 mm by size and sterilized by irradiation.

<2-3-3> Methods

Skin hair on the animal's back was removed and the skin was pasteurized with disinfectant after subjecting the animals to general anesthesia with Ketamine HCl (Ketara 10 mg/kg) and 2% Xylazine HCl (Rompun 0.15 ml/kg). After securing the space for the graft materials by incising the skin about 5 mm length and undermining the subcutaneous tissue, the bone fragments prepared by Example 2-3-2 were transplanted 1 cm apart from the incised site and sutured. After sacrificing 2 rats by cervical dislocation after 1, 2, 4, and 12 weeks transplantation, tissues surrounding the transplanted bone were extracted and fixed immediately with 10% neutrally buffered formaldehyde. After fixation for 2 days in the same fixing solution, the fragments were decalcified with 5% nitric acid and bisected from the center of them. Then, the bone fragments were dehydrated with ethyl alcohol, cleaned with xylene and embedded with paraffin. The paraffin-embedded tissues were sliced by 4 µm thickness and stained triply with Hematoxylin, Eosin and Gomori.

The results observed by the method were as following:

1) Optical observation

Any inflammatory symptom was not observed, and the grafted fragments were surrounded by thin and transparent tissues.

2) Microscopic observation

Since the grafted fragments were a cancellous bone, they were surrounded by granulation tissues at the multi-porous structure of them. Fibrous tissues were scanty and many blood vessels were found around and in the grafted fragments. Some giant multinucleated cells were found near the grafted fragments. Most of them were under decalcification on their surface and had reduced size due to decalcification by nitric acid.

Figure 2:
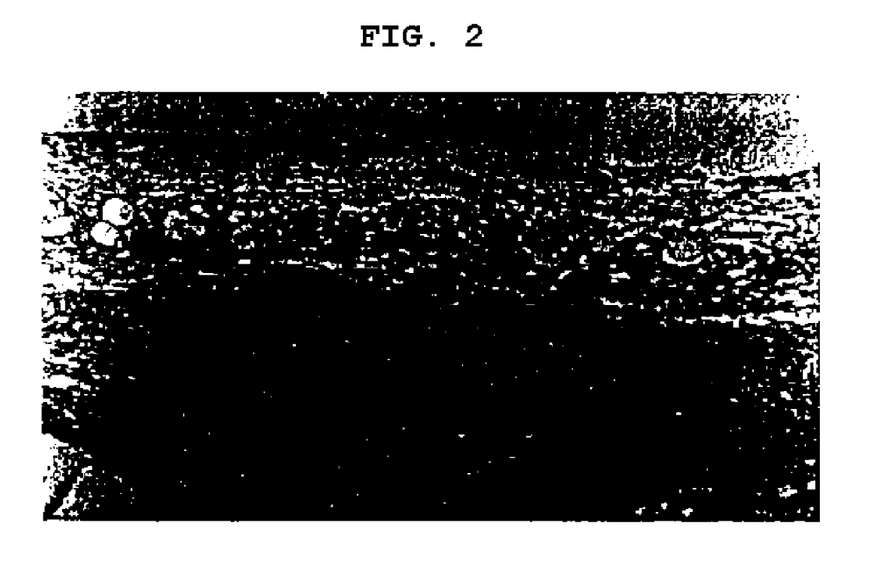
FIG. 2 and FIG. 3 are photographs of histological sectioned view of bone powder of the present invention after grafting the bone powder into the tissue.
Figure 3:
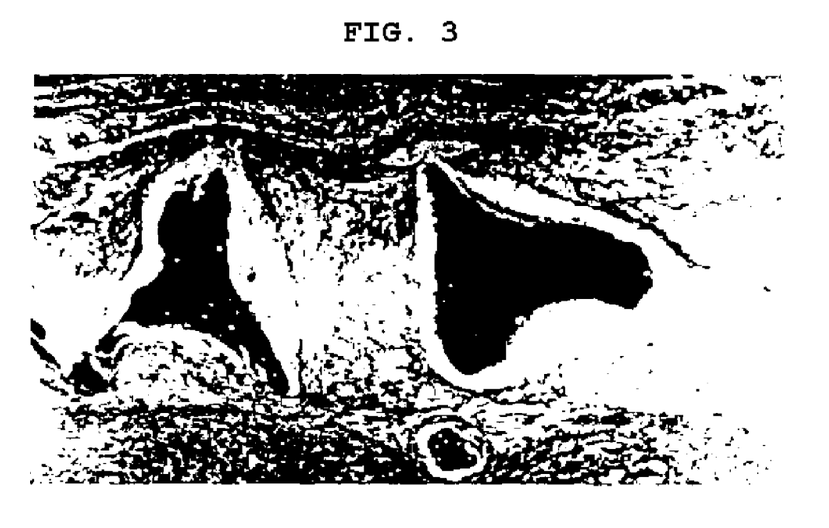

3) There was no inflammatory symptom after 1 week transplantation by optical observation. The grafted materials were histologically tegumentalized into the number of cells, exudates, granulation tissues and fibrous tissues (FIG. 2 and FIG. 3).

<2-4> Sensitization Test

In order to examine whether a skin sensitization might be occurred by application of patch, the probability of skin sensitization was tested by intradermal injection the bone powder extract into guinea pigs.

<2-4-1> Reagents

The bone powder extract was prepared by the method of Example 2-1-1.

<2-4-2> Test Animals

Male guinea pigs having 350-400 g of body weight were used as test animals and adapted to new habitat of laboratory 1 week before experiment.

<2-4-3> Preparation of Experiment

Hairs around flank and back of the animals were removed using animal clipper at the day before experiment. In case of intradermal injection, 0.1 ml of the bone powder extract was injected to each part. In case of topical application, filter paper was cut into appropriate size (2×4 cm) and fully soaked in the bone powder extract. After that, the filter paper was attached to the shaved region of guinea pig (back region), covered with cellophane paper to prevent evaporation of the bone powder extract and fixed with occlusive dressing.

<2-4-4> Preparatory Experiment

A preparatory experiment was performed to determine the concentration of the bone powder extract used in the main experiment.

10% of the bone powder extract was made by mixing 20% concentration of the bone powder extract prepared by Example 2-1-1 and Freund's complete adjuvant capable to promote the sensitization reaction in the ratio of 1:1. After that, 10%, 1% and 0.1% concentration of the bone powder extract was prepared by diluting 10% bone powder extract, and used for the experiment.

6 guinea pigs were divided into 3 groups each of which contained 2 guinea pigs. Then, 10, 1, 0.1% of the bone powder extract was injected into each group intradermally. After applicating 3 concentrations of the bone powder extract topically to the back of 3 groups of guinea pigs, adhesive plaster and patch were removed at 24 hours. Erythema and edema appeared at the injected or applied regions were measured by the criteria of grade decision method described in the Table 2. Since there was no changes to the animals injected 10% of extract of the bone powder (2 guinea pigs) and applied it topically (3 guinea pigs), the grade was 0, so 10% of extract of the bone powder was used for the further experiment.

TABLE 2

Grade decision according to the skin response

| Response | Numerical grading |
|---|---|
| Erythema and eschar formation | |
| No erythema | 0 |
| Slight erythema | 1 |
| Well-defined erythema | 2 |
| Moderate erythema | 3 |
| Severe erythema to slight eschar formation | 4 |
| Oedema formation | |
| No oedema | 0 |
| Slight oedema | 1 |
| Well-defined oedema | 2 |
| Moderate oedema | 3 |
| Severe oedema | 4 |

Important point;
1. Other changes around skin regions might be recorded and reported.

As a result of performing the preparatory experiment to determine the concentration of the bone powder extract which would be used in the main experiment, there was no changes to the animals injected or topically applied 10%, 1%, and 0.1% of the bone powder extract to each of them. When erythema and edema were determined by the criteria of grade decision described in the Table 2, the grade was 0. Therefore, it was determined to use 1 0% of the bone powder extract for the main experiment.

<2-4-3> Main Experiment 10 guinea pigs were used as sample group and 5 guinea pigs as control group.

Intradermal Induction Phase

Figure 4:
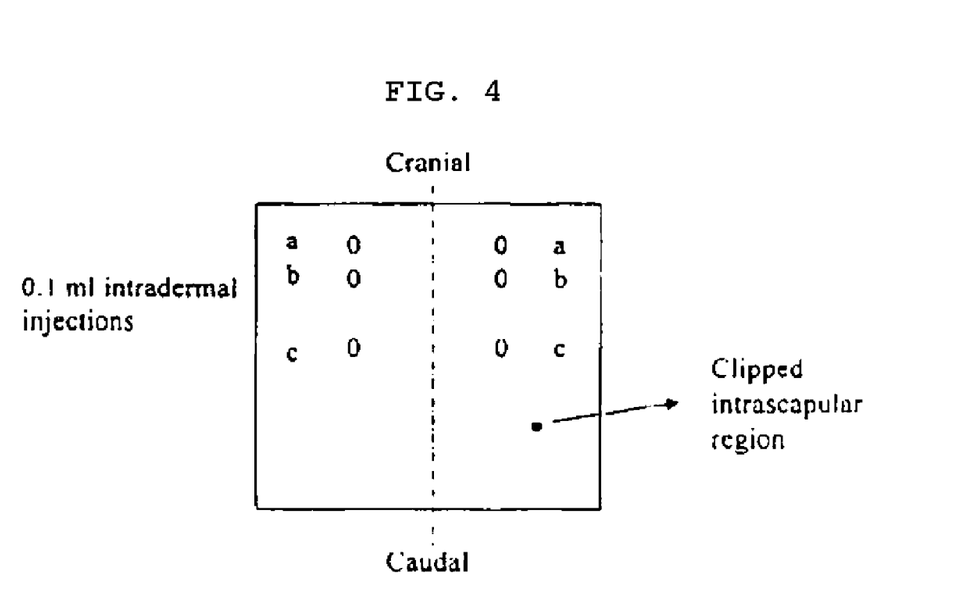
FIG. 4 is a schematic diagram showing subcutaneous injection point of bone powder reagent of the present invention in the guinea pig, wherein the bone powder reagent is prepared by shaking incubation at 37° C. water bath for 72 hours using saline as extraction solvent.

As shown in FIG. 4, 0.1 ml of each reagent solution (A, B, C) prepared as described below was injected intradermally to each region (a, b, c) located between both shoulder blades of shaved each guinea pig:

Mixture of Freund's complete adjuvant and distilled water in the ratio of 50:50 (v/v);

Only 10% of the bone powder extract to the sample group and only saline to the control group; and Mixture of Freund's complete adjuvant and 10% of the bone powder extract in the ratio of 50:50 (v/v) to the sample group and only mixture of Freund's complete adjuvant and saline in the ratio of 50:50 (v/v) ratio to the control group.

In accordance with the above method, 0.1 ml of each reagent solution (A, B, C) was serially injected intradermally to each region (a, b, c) located between both shoulder blades of the shaved each guinea pig, as shown in FIG. 1. After that, there were no inflammatory responses to all the 15 guinea pigs.

Topical Induction Phase

After 7 days of the intradermal induction phase test, 20 mm×40 mm filter paper soaked in 10% of the bone powder extract was applied to fully cover the injection site of each animal's shoulder blade. After that, occlusive dressing was treated to prevent evaporation of the bone powder extract. After removing the dressing and the patches at 48±2 hours, the response was observed. In case of the control group, all the other treatment was the same as the sample group except that saline was used instead of the bone powder extract.

As a result of observing the response according to the steps, edema of grade 1 was found at the 2 of 20 in A region, 2 of 20 in B region and 3 of 20 in C region, but there were no regions representing erythema. For the control group, saline was used instead of the bone powder extract. As a result of observing the responses after removing the dressing and patches, edema of grade 1 was appeared at the 2 of 10 in A region, 1 of 10 in B region and 2 of 20 in C region, but there were no regions representing erythema.

From these results, it was concluded that there was no sensitization response induced by the bone powder of the present invention during the topical induction phase.

Challenge Phase

After 7 days of the topical induction phase test, the main experiment to all the sample and control groups was performed. After injection of 0.1 ml 10% of the bone powder extract to the flank of each animal, the patch soaked in 10% of the bone powder extract was attached and the occlusive dressing was treated. After 24±2 hours later, the dressing and patch were removed and the responses were observed.

As a result, there were no edema and erythema in all 15 animals used in the experiment. So, it was confirmed that there was no sensitization reaction induced by the bone powder extract of the present invention during the challenge phase.

From the results of the experiments, it was found that there was no inflammatory reaction such as edema and erythema in all 15 animals of the sample and control group. Although there were some edemas of grade 1 in the topical induction phase, it could not be said as sensitization reaction since the control group also showed the same responses as the sample group. In addition, there was no inflammatory reaction such as edema and erythema in all 15 animals in the challenge phase. So, it was concluded that there was little inducing probability of the sensitization reaction by the bone powder extract of the present invention, since there was no sensitization reaction in the present experiment of maximum sensitization test constituting intradermal induction phase, topical induction phase and challenge phase.

<2-5> Aseptic Test

To confirm the safety and effectiveness of the bone powder of the present invention, aseptic test was performed by the following growth methods to check for the existence of any bacteria or fungi proliferation. According to the aseptic test of general experimental method in THE KOREAN PHARMACOPEIA($6^{th}$ edition), bacteria and fungi test was carried out by the direct inoculation.

<2-5-1> Strains

*E. coli* DH5α was used as bacterium, and several fungi were used by leaving Glu-peptone medium in the air and directly culturing (Table 3).

TABLE 3

| Microorganism strain | | |
|---|---|---|
| Strain | Description | Source |
| *E. coli* DH5α | SupE44 supF58 hsdS3($r_B m_B$)(Φ80lacZΔM15) hsdR17 recA1 endA1 gyrA96 thi-1 relA1 | Stratagene |

<2-5-2> Media and Reagents

The media and the composition used in the experiment were represented in the Table 4.

Brewe Thioglycollate Medium for aseptic test to detect microorganism was prepared by mixing beef infusion, sodium chloride, dipotassium phosphate, protease peptone, Bacto dextrose, Bacto agar, and Bacto methylene blue with 200 ml of water and dissolving in the water bath. After addition of sodium thioglycollate to the mixture, 40 ml of the mixture was separately added into test tube (25 mm×200 mm) and autoclaved at 121° C. for 20 minutes. After cooling the tubes at ambient temperature, it was used for the experiment. Glu-peptone medium for aseptic test to detect fungi was prepared by mixing $KH_2PO_4$, $MgSO_4$, peptone, yeast extract and glucose with 200 ml of water and 15 ml of the mixture was separately added into test tube (25 mm×200 mm) and autoclaved at 121° C. for 20 minutes. After cooling the tubes at ambient temperature, it was used for the experiment.

TABLE 4

| Chemical composition of the medium | |
|---|---|
| Brewe Thioglycollate Medium | |
| Beef Infusion | 500 g |
| Sodium Chloride | 5.0 g |
| Dipotassium Phosphate | 2.0 g |
| Protease Peptone | 10 g |
| Bacto Dextrose | 3.0 g |
| Bacto Agar | 0.5 g |
| Bacto Methlene Blue | 0.002 g |
| Sodium Thioglycollate | 0.5 g |
| Distilled Water | 1 L |
| Glu-peptone Medium | |
| $KH_2PO_4$ | 1.0 g |
| $MgSO_4$ | 0.5 g |
| Peptone | 5.0 g |
| Yeast extract | 2.0 g |
| Glucose | 20.0 g |
| Distilled Water | 1 L |

<2-5-3> Efficiency Test of the Medium

Brewe Thioglycollate Medium was kept at 30° C. for 5 days and Glu-peptone Medium at 25° C. for 13 days. After confirming that there were no turbidity, production of precipitant or other abnormalities, they were used. To test whether the media were in the optimal condition for the growth of microorganisms, it was confirmed that *E. coli* DH5α inoculated in Brewe thioglycollate Medium was grown and several fungi in Glu-peptone Media left in the air were directly grown.

<2-5-4> Preparation and Handling of a Bone Graft Material Solution

The bone graft materials used in the experiment were solid one having 0.425-0.524 mm of size. Some of them were suspended in the distilled water and adjusted their final concentration to be 1%. The bone graft material solution prepared as described above was added to the medium as Table 5 and used for tests (test tube No. 3-5, and 9). Some were directly used for the experiment by adding 0.4 g of the bone graft materials to test mediums (test tube No. 6, 7, and 10). All the procedures of the test were performed under aseptic condition.

TABLE 5

| Volume of the test bone graft materials solution | | | | | | | |
|---|---|---|---|---|---|---|---|
| | | Bacteria test | | | Fungi test | | |
| Indication | Collection | Per every test tube | | Number of test tubes | Per every test tube | | Number of test tubes |
| | | Test | Medium | | Test | Medium | |
| Above 1 g | About 1 g | 5 ml | 40 ml | 2 | 2 ml | 15 ml | 5 |

<2-5-5> Culture Conditions

For bacterial test, the bone graft material solution was mixed well with medium and incubated for 10 days at 30° C.

and for fungal test, incubated for 10 days at 25° C. Since 25 mm×200 mm test tube was used in the fungal test, 20-30° slopes were maintained during incubation.

After incubation, there was no growth of microorganisms in all the test tubes except the tubes (No. 2 and No. 8) for efficiency test of the medium (Table 6).

TABLE 6

|  | Fungal test | | | | | | Bacterial test | | | |
|---|---|---|---|---|---|---|---|---|---|---|
| Tube No. | 1 | 2 | 3 | 4 | 5 | 6 | 7 | 8 | 9 | 10 |
| Decision | X | ○ | X | X | X | X | X | ○ | X | X |

Tube No. 1: For efficiency test of the medium
Tube No. 2: For efficiency test of the medium (leaving in the air)
Tube No. 3-7: For bone graft material solution test
Tube No. 8: For efficiency test of the medium (inoculated with *E. coli*)
Tube No. 9-10: For bone graft material solution test From the test which confirmed biological safety and efficiency of the bone graft material of the present invention by detecting whether microorganisms (bacteria, fungi) existed or not, the following results were obtained:

There was no microorganism in the bone graft material solution.

There was no fungus in the bone graft material solution.

Therefore, it was concluded that the bone graft material of the present invention was suitable for bone grafting application according to aseptic test.

INDUSTRIAL APPLICABILITY

The bone graft materials prepared by the method of the present invention are free from lipid and organic materials and only have inorganic materials. In addition, the bone graft materials are biocompatible and do not cause immune responses in living body. Therefore, the bone graft materials of the present invention can be used for frames to provoke osteogenesis and bone morphogenesis. Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for preparing inorganic bone graft materials, said method consisting of:
   1) removing, from an animal, a compact bone from bone using a bone saw and obtaining a cancellous bone;
   2) making bone powder by pulverizing the cancellous bone minutely;
   3) washing the bone powder with distilled water;
   4) removing lipids from the washed bone powder using diethyl ether;
   5) removing diethyl ether from the bone powder using ethanol;
   6) washing the bone powder of step 5 to remove ethanol using distilled water;
   7) removing organic materials, including proteins present after the preceding steps, from the bone powder of step 6 using sodium hypochlorite and hydrogen peroxide;
   8) washing the bone powder of step 7 using distilled water; and
   9) lyophilizing the bone powder of step 8 with a freeze drier, thereby producing inorganic bone graft material, wherein the inorganic bone graft material is free from organic material.

2. The method according to claim 1, wherein the animal is a bovine.

3. A method for preparing inorganic bone graft materials, said method consisting of:
   1) deep freezing a bone from an animal;
   2) removing a compact bone from the bone using a bone saw to produce a bone free from a compact bone and obtaining a cancellous bone with a size between 1 mm×1 mm×1 mm to 30 mm×30 mm×30 mm by cutting the bone free from a compact bone;
   3) making bone powder by pulverizing the cancellous bone minutely;
   4) washing the bone powder using distilled water;
   5) removing lipids from the washed bone powder using diethyl ether;
   6) drying the bone powder of step 5 to remove diethyl ether in the hood, and separating it into a size selected from above 1.4 mm, to 1.4 mm, 0.6 to 1 mm, 0.425 to 0.6 mm, and below 0.425 mm;
   7) deep freezing the bone powder of step 6 having size of 0.6 to 1 mm and 0.425 to 0.6 mm, and further pulverizing the bone powder bigger than 1 mm minutely;
   8) removing lipids from the re-pulverized bone powder of step 7 using diethyl ether;
   9) drying the bone powder of step 8 to remove diethyl ether in the hood, and separating it into a size selected from above 1.4 mm, 1 to 1.4 mm, 0.6 to 1 mm, 0.425 to 0.6 mm, and below 0.425 mm;
   10) collecting the bone powder of step 9 having size of 0.6-1 mm and 0.425-0.6 mm;
   11) removing remaining diethyl ether from the frozen bone powder of step 7 and the bone powder of step 10 by washing with ethanol;
   12) washing the bone powder of step 11 with distilled water;
   13) removing organic materials, including proteins, from the bone powder by treating the washed bone powder of step 12 with sodium hypochlorite;
   14) further removing organic materials, including proteins present after the preceding steps, from the bone powder of step 13 by treating the bone powder with hydrogen peroxide and keeping the bone powder overnight in hydrogen peroxide;
   15) washing the bone powder of step 14 with distilled water; and
   16) removing moisture from the washed bone powder of step 15 by lyophilizing the bone powder with a freeze drier, thereby producing inorganic bone graft material, wherein the inorganic bone graft material is free from organic material.

4. The method according to claim 3, wherein the animal is a vertebrate.

5. The method according to claim 4, wherein the animal is a bovine.

* * * * *